(12) United States Patent
Kessler

(10) Patent No.: US 7,810,425 B1
(45) Date of Patent: Oct. 12, 2010

(54) SYSTEM FOR PROCESSING GRAINS, CARBOHYDRATES, SUGARS, AND OILSEEDS

(76) Inventor: Michael Kessler, P.O. Box 236, R.R. #2, Box 119, Ladoga, IN (US) 47954

( * ) Notice: Subject to any disclaimer, the term of this patent is extended or adjusted under 35 U.S.C. 154(b) by 1190 days.

(21) Appl. No.: 10/916,702

(22) Filed: Aug. 12, 2004

(51) Int. Cl.
C12C 11/00 (2006.01)
C12G 1/02 (2006.01)

(52) U.S. Cl. .......................... 99/276; 99/277; 210/287

(58) Field of Classification Search .................. 99/276, 99/277; 210/251, 287, 679, 435
See application file for complete search history.

(56) References Cited

U.S. PATENT DOCUMENTS

| | | | |
|---|---|---|---|
| 2,241,375 A | 5/1941 | Campbell | |
| 3,622,511 A | 11/1971 | Pizzo et al. | |
| 3,918,521 A * | 11/1975 | Snavely et al. | 166/272.3 |
| 3,933,600 A | 1/1976 | Dodge et al. | |
| 4,045,338 A * | 8/1977 | Miyamoto et al. | 210/679 |
| 4,309,254 A | 1/1982 | Dahlstrom et al. | |
| 4,328,074 A | 5/1982 | Standiford | |
| 4,358,536 A | 11/1982 | Thorsson et al. | |
| 4,381,220 A | 4/1983 | Standiford | |
| 4,462,342 A | 7/1984 | Welden | |
| 4,522,920 A | 6/1985 | Thorsson et al. | |
| 4,539,076 A | 9/1985 | Swain | |
| 4,566,947 A | 1/1986 | Tsuruta | |
| 4,612,286 A * | 9/1986 | Sherman et al. | 435/157 |
| 4,626,321 A | 12/1986 | Grethlein et al. | |
| 4,636,284 A | 1/1987 | English et al. | |
| 4,660,511 A | 4/1987 | Anderson | |
| 5,273,682 A * | 12/1993 | Danzik | 516/113 |
| 5,294,304 A | 3/1994 | Kano et al. | |
| 5,416,245 A * | 5/1995 | MacGregor et al. | 568/697 |
| 6,135,063 A | 10/2000 | Welden | |
| 6,267,309 B1 * | 7/2001 | Chieffalo et al. | 241/17 |
| 6,338,337 B1 | 1/2002 | Panz et al. | |
| RE37,653 E | 4/2002 | Anderson | |
| 6,368,552 B1 * | 4/2002 | Shimura et al. | 422/14 |
| 7,297,236 B1 | 11/2007 | Vander Griend | |
| 2003/0019736 A1 | 1/2003 | Garman | |
| 2005/0266539 A1 | 12/2005 | Hochberg et al. | |
| 2007/0000769 A1 | 1/2007 | Brown | |
| 2007/0051513 A1* | 3/2007 | Heins | 166/265 |
| 2007/0190626 A1 * | 8/2007 | Wilkening et al. | 435/161 |
| 2007/0256920 A1 | 11/2007 | Kanauchi et al. | |
| 2008/0032394 A1* | 2/2008 | Offerman et al. | 435/290.1 |

OTHER PUBLICATIONS

"Water Energizers® Facts" from Water Energizers, Inc.; copyright 2001; http://www.waterenergizers.com; 1 page.
Images and Figs. 1 and 2 from Water Energizers, Inc; http://www.waterenergizers.com/images/Fig1_2_lrg.gif; 1 page.

* cited by examiner

Primary Examiner—Reginald L Alexander
(74) Attorney, Agent, or Firm—Baker & Daniels LLP

(57) ABSTRACT

The present invention includes a method apparatus and system for processing grains, sugars, carbohydrates and oilseeds. Specifically, the present invention includes a method and apparatus for fermenting carbohydrates from grains to produce ethanol.

10 Claims, 7 Drawing Sheets

US 7,810,425 B1

SYSTEM FOR PROCESSING GRAINS, CARBOHYDRATES, SUGARS, AND OILSEEDS

FIELD OF THE INVENTION

The present invention is related to the field of industrial processing, particularly the processing of grains, oilseeds, sugars, and carbohydrates.

BACKGROUND AND SUMMARY

Conventional methods and systems for fermenting and or enzymatically processing carbohydrates such as grains to produce products such as ethanol generally involve producing steam with a fire tube boiler and heating the grain or carbohydrates with steam while in the presence of enzymes, which convert the carbohydrates to sugars, and yeast or bacteria that convert the sugars to ethanol and carbon dioxide. This process is carried out in the absence of oxygen. Similarly, non-carbohydrate derived sugars such as xylose can be converted to ethanol and carbon dioxide while in the presence of yeast. The exhaust product generated from the fire tube boiler contains various nitrogen and sulfur based oxides ($NO_x$ and $SO_x$) that may be removed via a scrubber or are exhausted to the atmosphere. Due to environmental regulations, removal of a portion of the $NO_x$ and $SO_x$ present in the exhaust may be required in some areas.

DETAILED DESCRIPTION OF THE DRAWINGS

Figure 1:
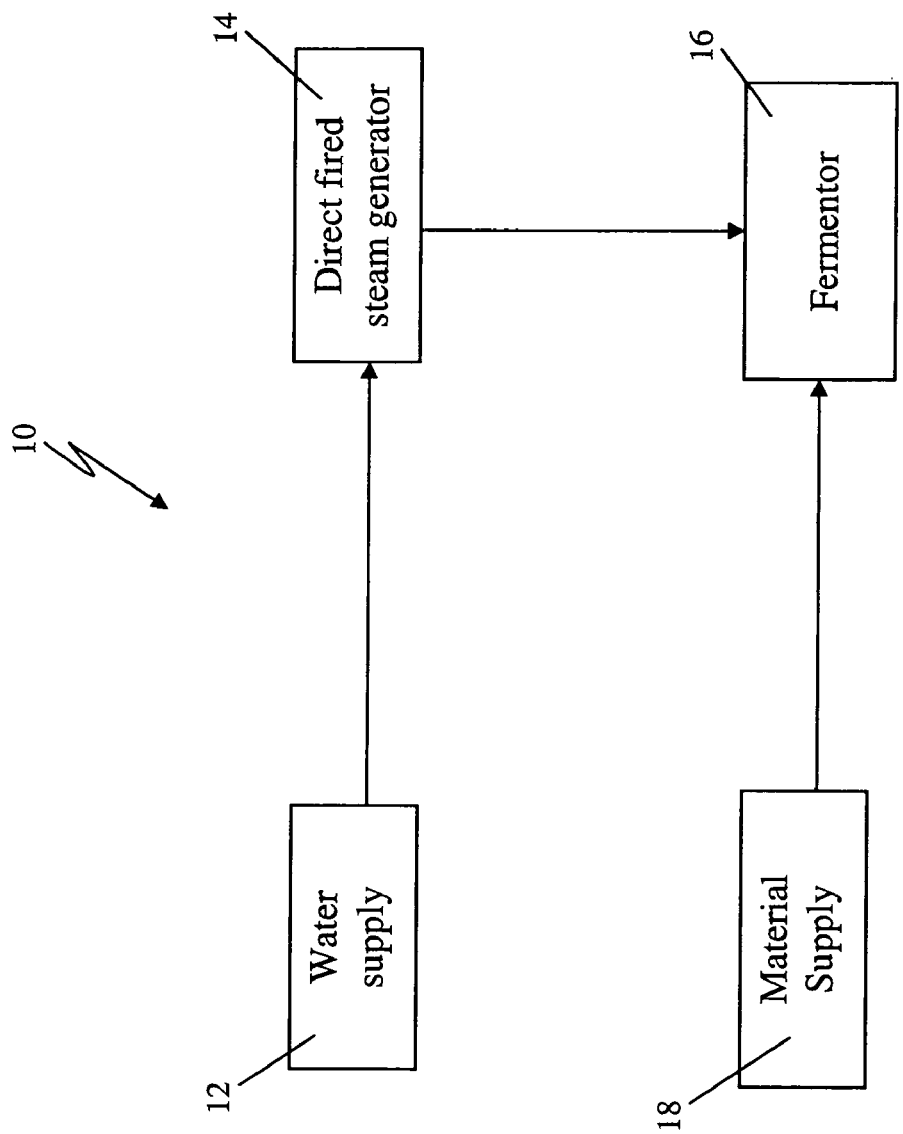
FIG. 1 is a flow chart of one embodiment of a fermentation system for a carbohydrate processing plant.

While the invention is susceptible to various modifications and alternative forms, exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

An apparatus for fermenting carbohydrates such as grain is shown in FIG. 1. In this exemplary embodiment, system 10 is configured to ferment grain to produce ethanol. As discussed above, conventional methods of processing grain to produce ethanol involve heating the grain, which has been ground, in the presence of water, enzymes, and yeast while in the absence of oxygen. System 10 includes a water supply 12, a direct fired steam generator 14, a fermentor 16, and a material supply 18. Water supply 12 supplies water from a well, a recycle stream, a utility connection, or any other suitable water source to direct fired steam generator 14. Direct fired steam generator 14 heats the water to produce steam. In alternative embodiments, a super heater can be positioned downstream of the direct fired steam generator to increase the temperature and pressure of the steam produced. Exemplary direct fired steam generators are described in U.S. Pat. Nos. 4,462,342 and 6,135,063 to Welden, the disclosure of each is expressly incorporated by reference herein. In a direct fired steam generator the flame or burner is submerged in or directly contacts water to produce steam. Therefore, the steam produced includes the exhaust products of combustion such $NO_x$ and $SO_x$.

Figure 2:
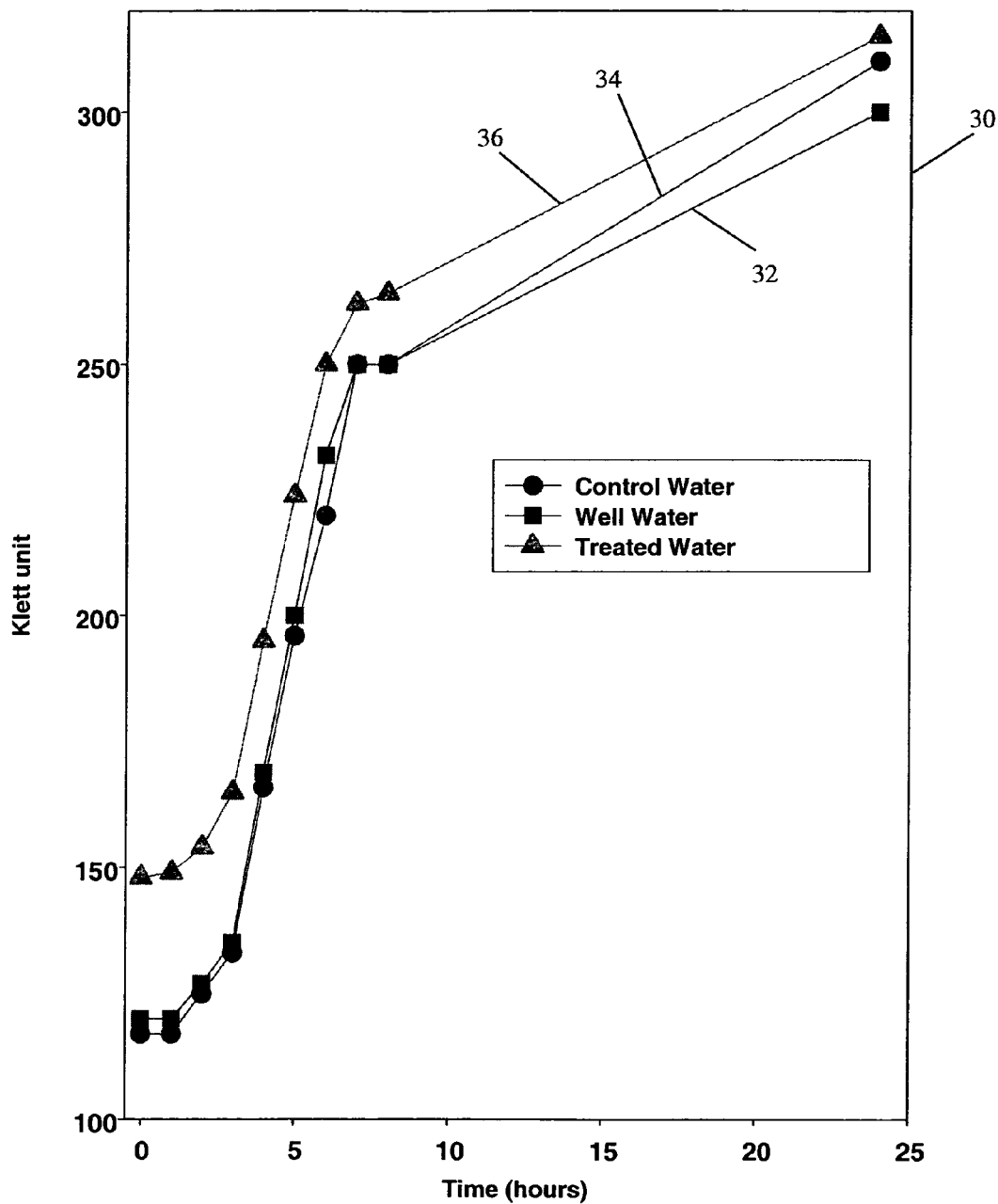
FIG. 2 is a graph depicting the growth of 424A(LNH-ST) yeast on YEPD made with control water, YEPD made with well water, and YEPD made with treated well water.
Figure 3:
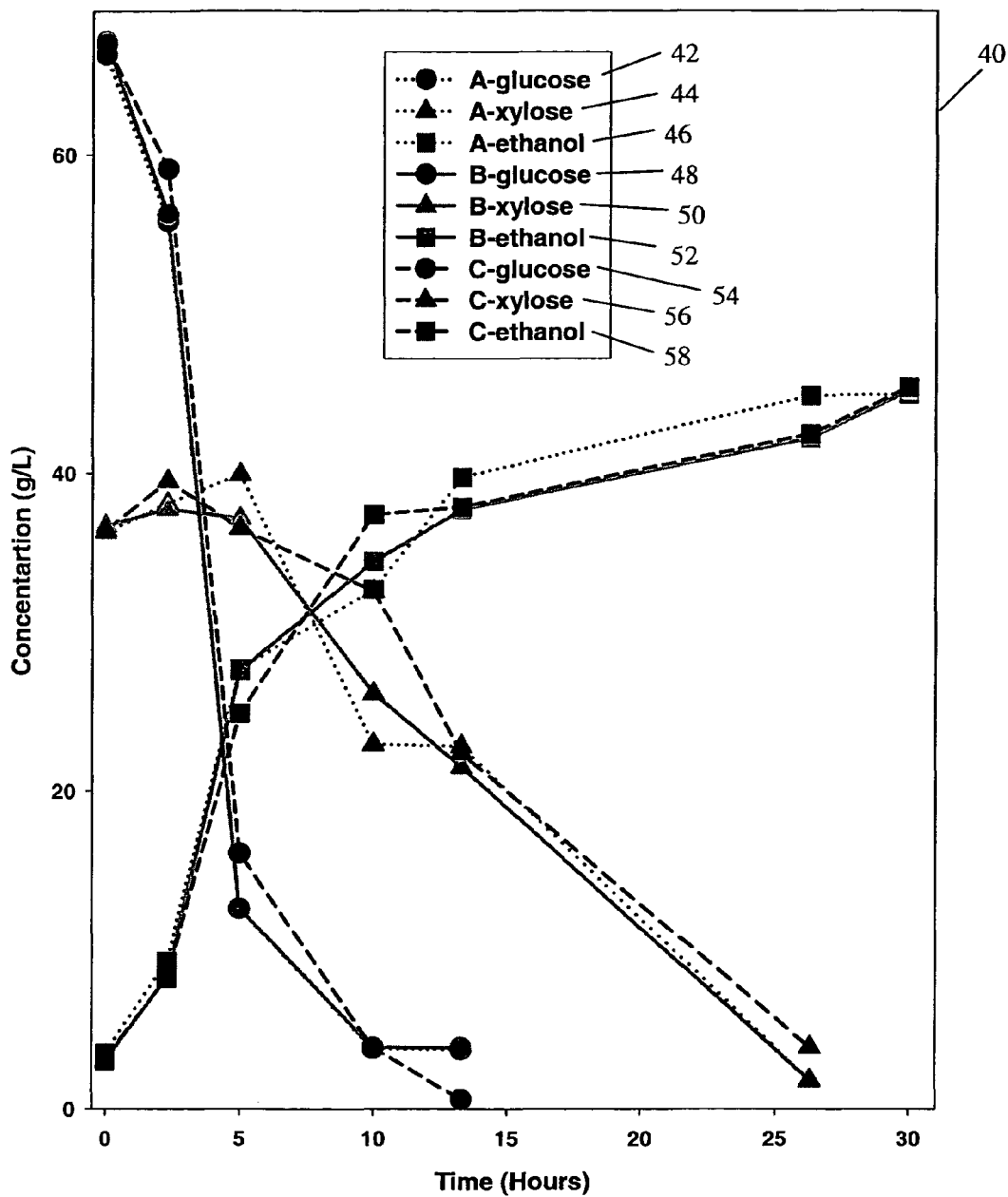
FIG. 3 is a graph depicting data from an experiment on co-fermentation of glucose and xylose added to YEP medium made from before (B) (well) and after (A) (well treated) water; and control (C), made from water from our laboratory by 424A(LNH-ST).

The steam generated by direct steam fired generator 14 is directed to fermentor 16. In other embodiments, fermentor 16 may be a reactor, processor, or any other suitable processing device. The product, in this example ground grain, is supplied to the fermentor by material supply 18. A mixture containing enzymes and yeast is added to the product which has been ground up, heated, and cooled. Steam that contains exhaust components from the direct fired steam generator 14 is then delivered into the fermentor 16. Research indicates microflora such as yeast grow and perform well in media which include nutrients such as sulfur and nitrogen. The $NO_x$, $SO_x$, and other exhaust components present in the steam provide nutrients to the yeast to support growth and conversion of glucose into ethanol as shown in FIGS. 2 and 3, which are described below. During the fermentation process, $CO_2$ and ethanol are produced. Downstream processes (not shown) separate and purify the components remaining after fermentation.

In another embodiment of system 10, the components and method of system 10 are implemented as an industrial plant. In yet another embodiment, system 10 is implemented as a small scale laboratory system. It should by understood that multiple fermentors utilized in a continuous or batch process could also be used. In a further embodiment, system 10 is used to convert sugars such as xylose to ethanol and carbon dioxide.

Referring now to FIG. 2, a graph 30 depicting Klett units (a measurement of growth) versus time in hours for growth of 424A(LNH-ST) (a strain of yeast) in three different YEPD mixtures is shown. Data set 32 is representative of measurements of growth of 424A(LNH-ST) in a mixture of YEPD and well water. The well water used was untreated. Data set 34 is representative of measurements of growth of 424A(LNH-ST) in YEPD. Data set 36 is representative of measurements of growth of 424A(LNH-ST) in a mixture of YEPD and treated water. Treated water is condensate formed from steam produced by direct fired steam generator. As discussed above, exhaust components such as $NO_x$ and $SO_x$ are present in the treated water. As indicated by data set 36, the treated water mixture produced greater growth of 424A(LNH-ST) then either well water or YEPD alone. The exhaust components in the treated water act as nutrients for the yeast to promote growth.

Referring now to FIG. 3, a graph 40 depicting data recorded during a co-fermentation of glucose and xylose by 424A(LNH-ST) with three different mediums is shown. The graph 40 indicates measurements of concentrations (g/L) of glucose, xylose, and ethanol in the three mediums over time during the fermentation process. Data sets 42, 48, and 54 are representative of the concentrations of glucose in a mixture of YEPD and treated water, a mixture of YEPD and well water, and a mixture of YEPD and distilled control water, respectively. Data sets 44, 50, and 56 are representative of concentrations of xylose in the mixture of YEPD and treated water, the mixture of YEPD and well water, and the mixture of YEPD and distilled control water, respectively. Data sets 46, 52, and 58 are representative of concentrations of the resulting ethanol in the mixture of YEPD and treated water, the mixture of YEPD and well water, and the mixture of YEPD and distilled control water, respectively.

As shown in graph 40, the concentration of glucose in all three mediums falls sharply during the first ten hours as the yeast (424A(LNH-ST)) converts the glucose to ethanol. The concentration of xylose increases briefly and then drops after about five hours in all three mediums. The concentration of ethanol is higher from about thirteen hours to about twenty-seven hours in the medium composed of the mixture of treated water and YEPD as shown by data set 46. Graph 40 indicates that the yeast in the YEPD and treated water (water including the exhaust components) mixture produced a higher concentration of ethanol for an extended period during the conversion of glucose and xylose to ethanol than the YEPD and YEPD and well water mixtures.

The experiments conducted regarding yeast growth and conversion rate, which are illustrated in FIGS. 2 and 3, indicate that the treated water that was produced by the direct fired steam generator increases the growth and performance of the yeast. Yeast growth during fermentation is supported by the presence of the exhaust components present in the steam produced by the direct fired steam generator. Emissions of the exhaust components are also reduced as a result of the direct fired steam generator and of usage of the exhaust components by the yeast. It should be understood by one having ordinary skill in the art that other yeast strains, unicellular organisms, and bacteria could be also used is this process and would exhibit similar results.

In another embodiment, the direct fired steam generation system is used in a carbohydrate processing plant that includes a fermentation process. As would be apparent to one having ordinary skill in the art, the direct fired steam generator and resulting water and steam including exhaust components could be used in any fermentation process to improve the efficiency of the process. In another embodiment, the direct fired steam generation system is used in an oilseed processing plant to increase the efficiency of the heating process and reduce emissions.

Figure 4:
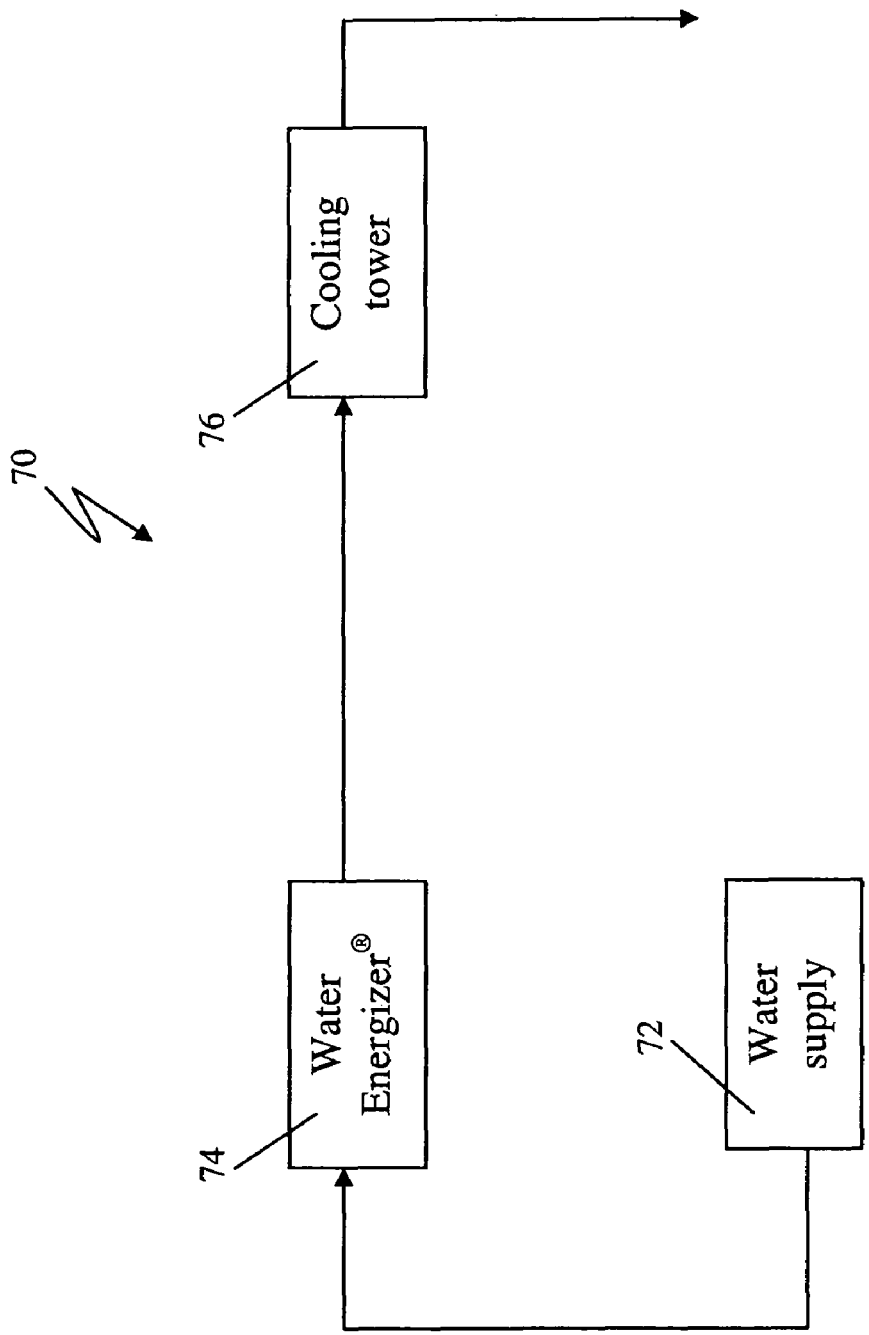
FIG. 4 is a flow chart depicting one embodiment of a water treatment system of the present invention.

Referring now to FIG. 4, one exemplary embodiment of a water treatment system 70 for a grain processing plant using system 10, described above, is shown. Water treatment system 70 includes a water supply 72, a water processor 74, a cooling tower 76, and appropriate piping to transport the water through the system. Water supply 72 includes treated water (which includes exhaust components) from the direct fired steam generator and or condensate. Water from other industrial processes, well water, utility supplied water, or any other suitable water source may supply water to be mixed with the treated water. Water is piped from water supply 72 to water processor 74. Water processor 74 is a non-chemical, non-magnetic in-line water treatment system such as Water Energizers®, a type of wet electrolysis device, which is produced by Water Energizers, Inc. in Jeffersonville, Ind. The water processor can be positioned directly upstream within piping leading to components using water such as a direct fired stream generator, a cooler tower, a wet scrubber, etc. Water processor 74 processes otherwise harmful chemicals from the water that may cause corrosion and scale in the cooling tower. After passing through water processor 74, the water is piped to cooling tower 76 where it is cooled. After passing through cooling tower 76, the water can be disposed of, piped to a recycle stream, piped to another process, or used for any other suitable purpose.

Although water treatment system 70 can be implemented in any apparatus or plant to remove corrosive components from water prior to entry cooling tower 76, the water processor is calibrated to process the exhaust components of the treated water produced by the direct fired steam generator. Without the water processor, a buildup of corrosive materials in the cooler tower caused by the exhaust components is possible.

Figure 5:
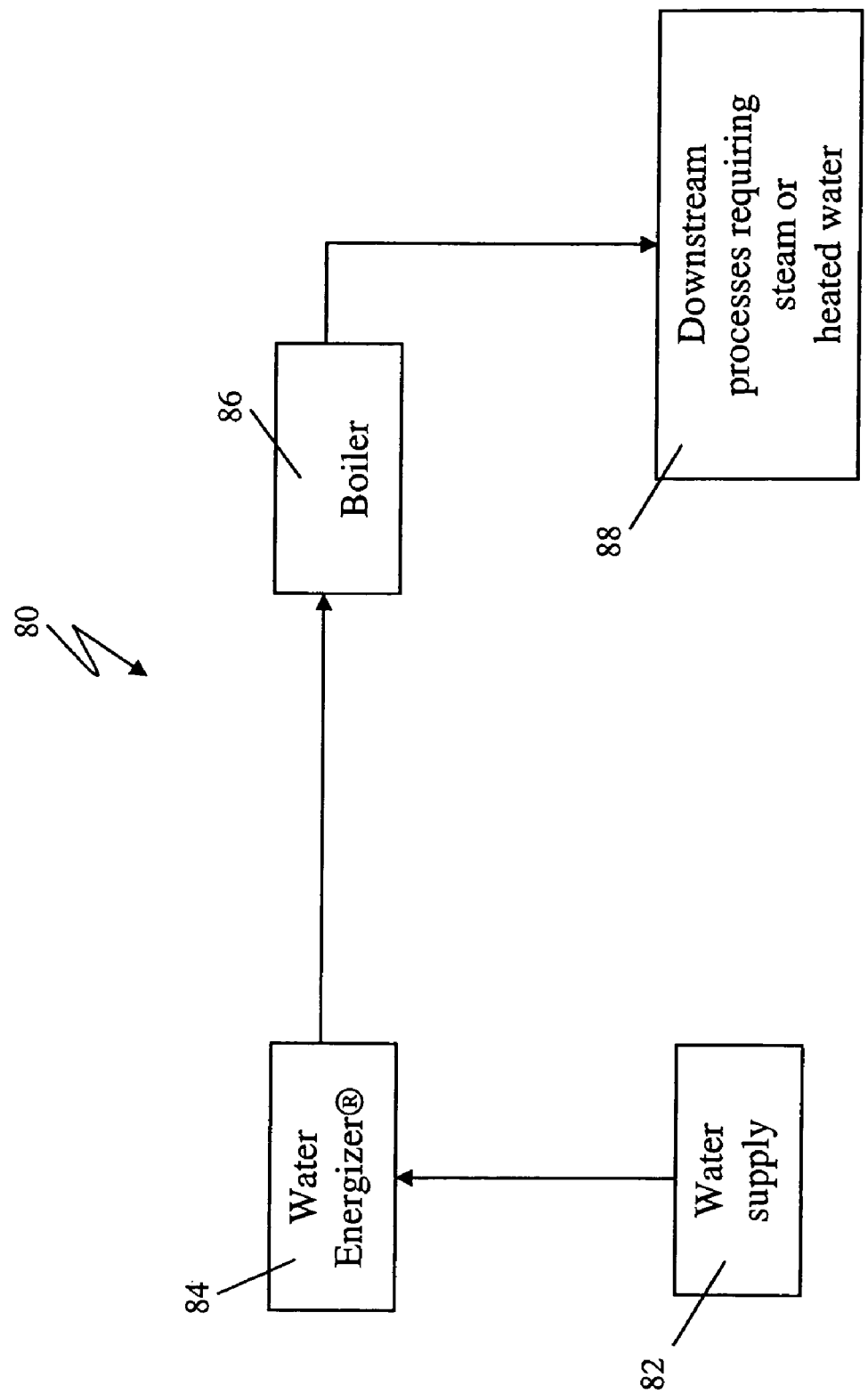
FIG. 5 is a flow chart depicting one embodiment of a water treatment system of the present invention.

Referring to FIG. 5, another exemplary embodiment of water treatment system 80 for a grain processing plant using system 10, described above, is shown. Water treatment system 80 includes a water supply 82, a water processor 84, a boiler 86, downstream processes 88 requiring steam or heated water, and appropriate piping to transport the water. Boiler 86 supplies steam and/or heated water to downstream processes 88 requiring steam or heated water. Water treatment system 80 is similar to water treatment system 70 with the exception that cooling tower 76 has been replaced by boiler 86 and downstream processes 88. Water supply 72 includes treated water (which includes exhaust components) from the direct fired steam generator or condensate return. Water from other industrial processes, well water, utility supplied water, or any other suitable water source can be mixed with the treated water. Water processor 84 serves the same purpose as water processor 74 in FIG. 5 of removing corrosive and scaling elements present in the treated water. If the exhaust components were not removed from the water supply to the boiler, corrosive deposits could form within the boiler 86. In alternative embodiments, boiler 86 can be a fuel cell or a direct fired steam generator.

Figure 6:
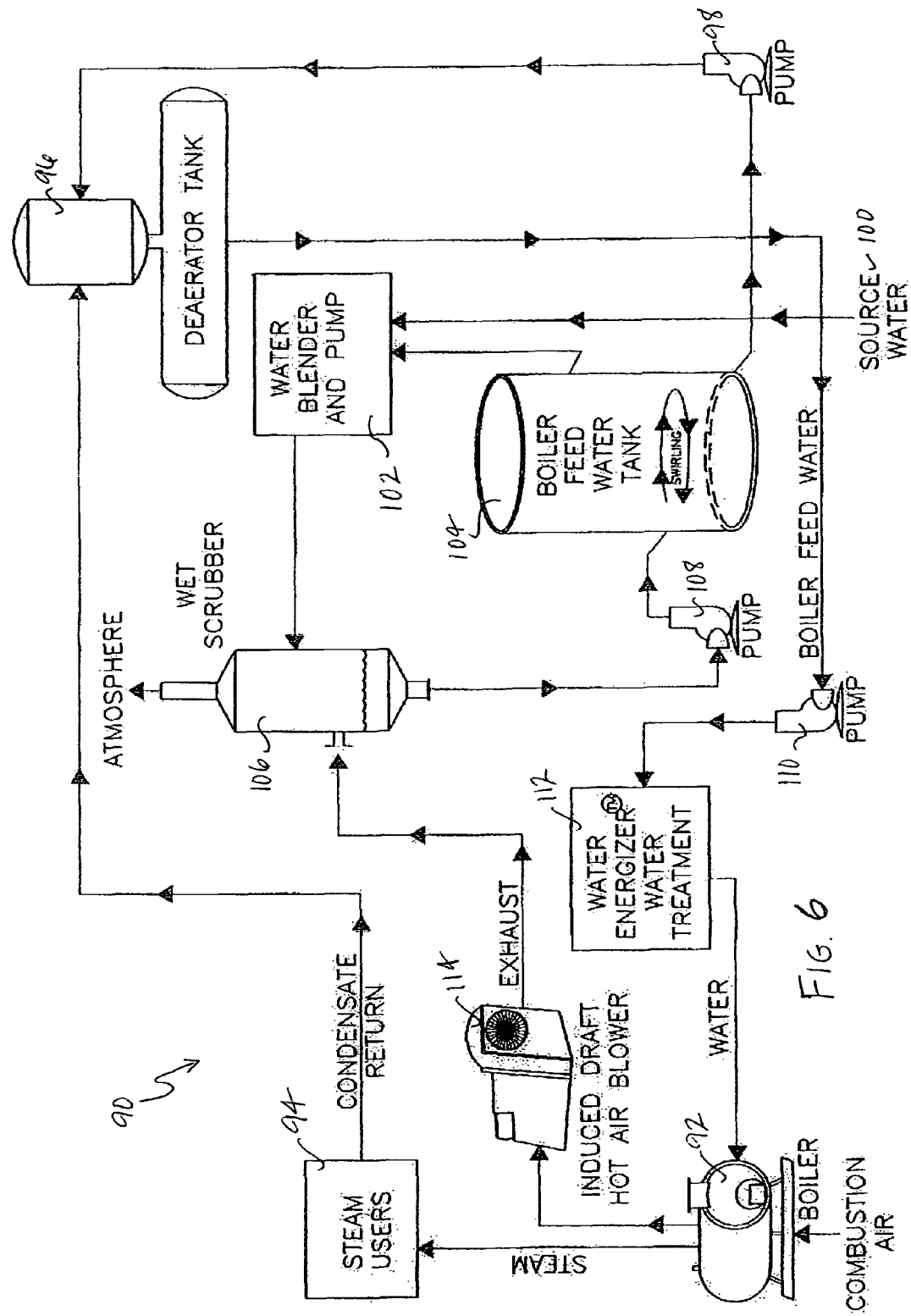
FIG. 6 is a flow chart depicting one embodiment of an exhaust heat recovery with a return system.

Referring new to FIG. 6, one exemplary embodiment of an exhaust heat return system 90 that can be used in a grain processing apparatus such as the one described above is shown. Heat return system 90 recovers heat from exhaust produced by boiler, steam generators, fuel cells, or any other suitable heat source. In the illustrated embodiment, heat return system 90 includes a boiler 92 which receives air for combustion and water to produce steam. Boiler 92 outputs steam to steam users 94 and exhaust from combustion to induced draft hot air blower 114. Steam users 92 may include any process requiring steam. Condensate is returned from the steam users and piped to deaerator tank 96 which removes air in the condensate. Exhaust from boiler 92 is transported to wet scrubber 106 by induced draft hot air blower 114.

Wet scrubber 106 receives exhaust from boiler 92 and water from blender 102. In wet scrubber 106, water is mixed with the exhaust to remove exhaust components such as $NO_x$ and $SO_x$ which are dissolved in the water to produce treated water. The remaining gas is vented to the atmosphere and the treated water is pumped into boiler feed water tank 104 by pump 108. Water blender 102, which supplies water to wet scrubber 106, blends water from boiler feed water tank 104 and water source 100 to raise the temperature of the water from the water source 100. Water source 100 could be a well, utility, recycle stream, or any other suitable water source.

Boiler feed water tank 104, which is described in detail below, continuously circulates water from wet scrubber 106 to maintain a homogenous mixture. Boiler feed water tank 104 includes at least one outlet to the water blender 102 and one outlet to pump 98 which pumps the treated water to deaerator tank 96. Deaerator tank 96 removes any air present in or dissolved in the water. Deaerator tank supplies water to pump 110 which pumps the treated water through water processor 112 to boiler 92. Water processor 112 removes corrosive chemicals present in the treated water that could corrode the boiler 92.

Figure 7:
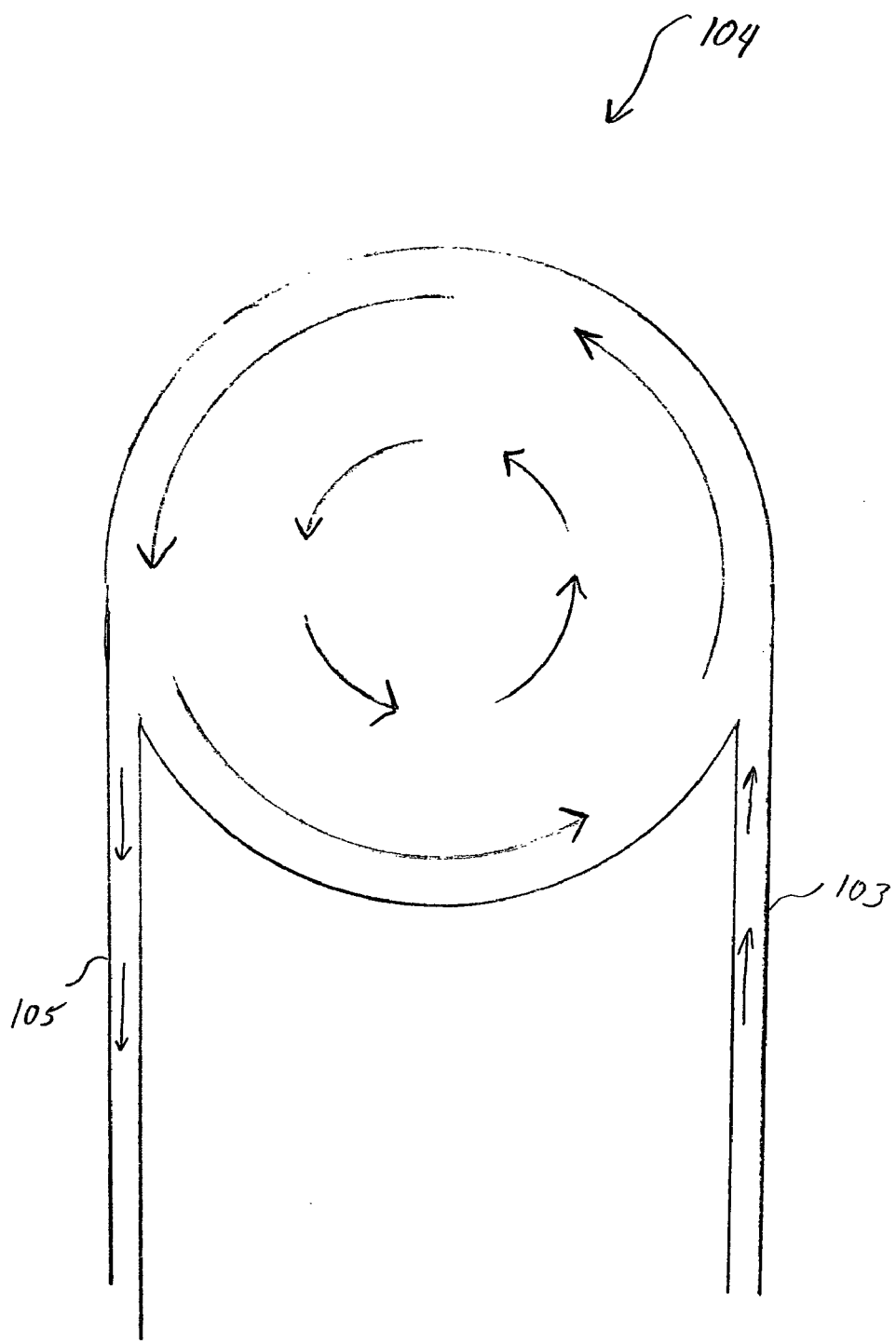
FIG. 7 is a top view of one embodiment of the boiler feed water tank shown in FIG. 6.

A top view of one embodiment of boiler feed water tank 104 is shown in FIG. 8. In this exemplary embodiment, tank 104 is cylindrically shaped and configured to stand or be mounted in an upright position as shown in FIG. 6. Inlet stream 103 is positioned in tank 104 tangentially relative to the circular profile of the tank 104. Similarly, outlet stream 105 is also positioned tangentially relative to the circular profile of tank 104. As shown in FIG. 7, the tangential positioning of the inlet 103 and outlet 105 create a swirling turbulent environment in tank 104, which promotes mixing of solids and liquids present in tank 104. The mixing properties of the tank 104 help maintain a homogenous mixture or solution in tank 104. In one embodiment of tank 104, inlet 103 and outlet 105 are vertically spaced apart along the cylindrical length of tank 104 to promote mixing. Although tank 104 is shown with only a single inlet and outlet, any suitable number of inlets and outlets could be positioned in tank 104. In the illustrated embodiment, the developed flow pattern has a counter-clockwise swirling motion, however in other embodiments the flow of the inlet and outlet could be reversed to promote a clockwise swirling motion.

While the invention has been illustrated and described in detail in the drawings and foregoing description, such illustration and description is to be considered as exemplary and not restrictive in character, it being understood that only exemplary embodiments have been shown and described and that all changes and modifications that come within the spirit of the invention and the attached claims are desired to be protected.

The invention claimed is:

1. An apparatus for processing at least one member selected from the group consisting of grain, oilseed, sugar, and carbohydrate, the apparatus including:
 a water source configured to supply water;
 a heat source configured to heat the water, wherein the heat source is a direct fired steam generator, wherein the direct fired steam generator provides exhaust products of combustion into the water to generate steam including the exhaust products of combustion, wherein the exhaust products of combustion include $NO_x$ and $SO_x$;
 a water processor coupled between the water source and the heat source, the water processor being configured to process and neutralize at least one chemical present in the water; and
 a fermentor for utilizing the steam, a product, and a mixture, where the steam, the product, and the mixture interact to produce at least one member selected from the group consisting of ethanol, lactic acid, and citric acid, and
 an induced draft hot air blower which transports a portion of the exhaust products of combustion to a wet scrubber,
 the product including at least one member selected from the group consisting of the grain, the oilseed, the sugar, and the carbohydrate,
 the mixture including at least one enzyme and yeast.

2. The apparatus of claim 1, wherein the water processor is configured to process a plurality of chemicals from the water.

3. The apparatus of claim 1, further comprising piping configured to supply the water from the water source to the heat source, the water processor positioned within piping.

4. The apparatus of claim 1, wherein the heat source is a boiler.

5. The apparatus of claim 1, wherein the water processor is a non-chemical, non-magnetic, in-line water treatment system.

6. The apparatus of claim 1, further comprising piping configured to supply the water from the water source to the heat source, the water processor positioned within piping.

7. The apparatus of claim 1, wherein the heat source is a boiler.

8. The apparatus of claim 1, wherein the water processor is a non-chemical, non-magnetic, in-line water treatment system.

9. The apparatus of claim 1, wherein the chemical treated by the water processor is air.

10. An apparatus for processing at least one member selected from the group consisting of grain, oilseed, sugar, and carbohydrate, the apparatus including:
 a water source configured to supply water;
 a heat source configured to heat the water, wherein the heat source is a direct fired steam generator, wherein the direct fired steam generator provides exhaust products of combustion into the water to generate steam including the exhaust products of combustion, wherein the exhaust products of combustion include $NO_x$ and $SO_x$;
 a water processor coupled between the water source and the heat source, the water processor being configured to process at least one chemical present in the water;
 a fermentor for utilizing the steam, a product, and a mixture, where the steam, the product, and the mixture interact to produce at least one member selected from the group consisting of ethanol, lactic acid, and citric acid, and
 an induced draft hot air blower which communicates a portion of the exhaust products of combustion to a wet electrolysis device,
 the product including at least one member selected from the group consisting of the grain, the oilseed, the sugar, and the carbohydrate,
 the mixture including at least one enzyme and yeast.

* * * * *

UNITED STATES PATENT AND TRADEMARK OFFICE
CERTIFICATE OF CORRECTION

| | | |
|---|---|---|
| PATENT NO. | : 7,810,425 B1 | Page 1 of 1 |
| APPLICATION NO. | : 10/916702 | |
| DATED | : October 12, 2010 | |
| INVENTOR(S) | : Michael Kessler | |

It is certified that error appears in the above-identified patent and that said Letters Patent is hereby corrected as shown below:

In claim 1, column 5, line 47, "the water; and" should read --the water;--.

Signed and Sealed this
Fifteenth Day of February, 2011

David J. Kappos
*Director of the United States Patent and Trademark Office*